United States Patent
Kim et al.

(10) Patent No.: US 10,625,248 B2
(45) Date of Patent: Apr. 21, 2020

(54) CATALYST COMPOSITION FOR HYDROFORMYLATION AND HYDROFORMYLATION METHOD USING THE SAME

(71) Applicant: LG CHEM, LTD., Seoul (KR)

(72) Inventors: Tae Yun Kim, Daejeon (KR); Sung Shik Eom, Daejeon (KR); Da Won Jung, Daejeon (KR); Dong Hyun Ko, Daejeon (KR); Mi Young Kim, Daejeon (KR); Min Ji Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 368 days.

(21) Appl. No.: 15/504,477

(22) PCT Filed: Aug. 26, 2016

(86) PCT No.: PCT/KR2016/009519
§ 371 (c)(1),
(2) Date: Feb. 16, 2017

(87) PCT Pub. No.: WO2017/057849
PCT Pub. Date: Apr. 6, 2017

(65) Prior Publication Data
US 2019/0111416 A1 Apr. 18, 2019

(30) Foreign Application Priority Data
Sep. 30, 2015 (KR) .................. 10-2015-0137632

(51) Int. Cl.
*B01J 31/00* (2006.01)
*B01J 31/02* (2006.01)
(Continued)

(52) U.S. Cl.
CPC .......... *B01J 31/0264* (2013.01); *B01J 31/18* (2013.01); *B01J 31/186* (2013.01); *C07C 45/50* (2013.01);
(Continued)

(58) Field of Classification Search
None
See application file for complete search history.

(56) References Cited

U.S. PATENT DOCUMENTS

| 4,567,306 A | 1/1986 | Dennis et al. |
| 6,639,114 B2 | 10/2003 | Ahlers et al. |
| 2012/0059195 A1 | 3/2012 | Choi et al. |

FOREIGN PATENT DOCUMENTS

| CN | 1871199 A | 11/2006 |
| CN | 102741210 A | 10/2012 |

(Continued)

OTHER PUBLICATIONS

SciFinder Abstract for KR 2010-0019058 (Year: 2010).*
(Continued)

*Primary Examiner* — Yun Qian
(74) *Attorney, Agent, or Firm* — Dentons US LLP

(57) ABSTRACT

The present invention relates to a catalyst composition for hydroformylation and a hydroformylation method using the same, and more particularly to a catalyst composition for hydroformylation including a phosphoramidite ligand and a transition metal catalyst, and a hydroformylation method using the catalyst composition. In accordance with the present invention, provided are a catalyst composition for hydroformylation which increases productivity and provides superior catalytic activity and stability while lowering an n/i ratio in generated aldehyde upon hydroformylation of an
(Continued)

olefinic compound, and a method of hydroformylating an olefinic compound using the catalyst composition. [Representative Figure] FIG. 1

10 Claims, 1 Drawing Sheet

(51) Int. Cl.
*B01J 31/18* (2006.01)
*C07C 45/50* (2006.01)
*B01J 31/40* (2006.01)
*C07C 47/02* (2006.01)

(52) U.S. Cl.
CPC ...... *B01J 31/4038* (2013.01); *B01J 2231/321* (2013.01); *B01J 2531/82* (2013.01); *B01J 2531/821* (2013.01); *B01J 2531/822* (2013.01); *B01J 2531/825* (2013.01); *B01J 2531/827* (2013.01); *B01J 2531/828* (2013.01); *B01J 2531/84* (2013.01); *B01J 2531/842* (2013.01); *B01J 2531/847* (2013.01); *C07C 47/02* (2013.01)

(56) References Cited

FOREIGN PATENT DOCUMENTS

| CN | 103201036 A | | 7/2013 | |
|---|---|---|---|---|
| KR | 2010019058 | * | 2/2010 | ............ C08F 236/10 |
| KR | 10-2015-0023342 A | | 3/2015 | |
| KR | 10-2015-0090918 A | | 8/2015 | |
| KR | 10-1574071 B1 | | 12/2015 | |
| WO | 2015-011145 A | | 1/2015 | |

OTHER PUBLICATIONS

Lee et al. (Org. Letters, 2014, 16, 5490-5493, supporting information (Year: 2014).*
Lee, et al.: "Bicyclic Bridgehead Phosphoramidite (Briphos) Ligands with Tunable pi-Acceptor Ability and Catalytic Activity in the Rhodium-Catalyzed Conjugate Additions", XP055578584, Organic Letters, vol. 16, No. 20, pp. 5490-5493 (2014).
Lee, et al.: "Rhodium-Catalyzed Asymmetric 1,4-Addition of a,b-Unsaturated Imino Esters Using Chiral Bicyclic Bridgehead Phosphoramidite Ligands", XP055578599, Journal of the American Chemical Society, vol. 137, No. 35, pp. 11250-11253 (2015).
Kang, et al.: "Palladium-Catalyzed Dehydrative Cross-Coupling of Allylic Alcohols and N-Heterocycles Promoted by a Bicyclic Bridgehead Phosphoramidite Ligand and an Acid Additive", XP055578747, Organic Letters, vol. 18, No. 3, pp. 616-619 (2016).

* cited by examiner

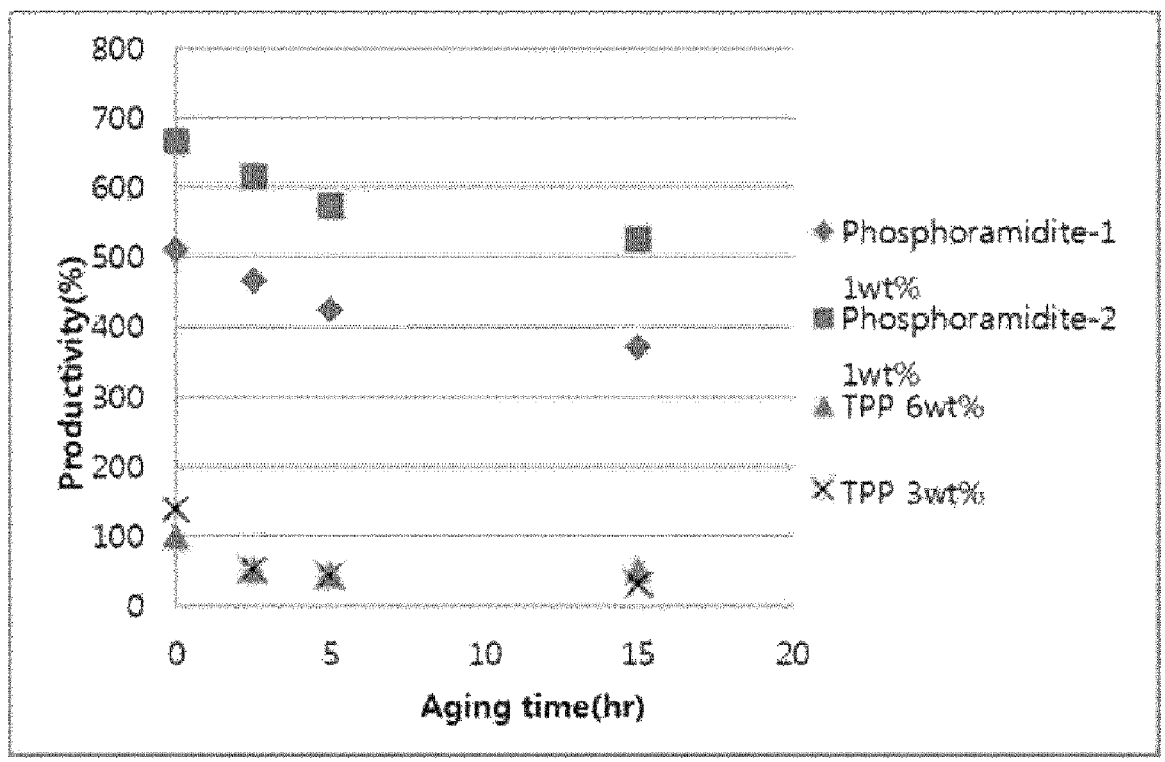

CATALYST COMPOSITION FOR HYDROFORMYLATION AND HYDROFORMYLATION METHOD USING THE SAME

CROSS-REFERENCE TO RELATED APPLICATION(S)

This application is a National Stage Entry of International Application No. PCT/KR2016/009519, filed Aug. 26, 2016, and claims the benefit of and priority to Korean Patent Application No. KR 10-2015-0137632, filed on Sep. 30, 2015, all of which are hereby incorporated by reference in their entirety for all purposes as if fully set forth herein.

TECHNICAL FIELD

The present invention relates to a catalyst composition for hydroformylation and a hydroformylation method using the same, and more particularly to a catalyst composition for hydroformylation which increases productivity and provides superior catalytic activity and stability while lowering an n/i ratio in generated aldehyde upon hydroformylation of an olefinic compound, and a method of hydroformylating an olefinic compound using the catalyst composition.

BACKGROUND ART

Hydroformylation, which was discovered by Otto Roelen in Germany in 1938, generates linear (normal) and branched (iso) aldehydes, a carbon number of which is increased by one, by reacting various olefins with carbon monoxide (CO) and hydrogen ($H_2$), which are often referred to as synthesis gases, in the presence of a homogeneous organometallic catalyst and ligand.

Hydroformylation reaction, commonly known as oxo reaction, is an industrially important homogeneous catalytic reaction. Through such oxo reaction, various aldehydes including alcohol derivatives are produced throughout the world.

Various aldehydes synthesized by oxo reaction may be oxidized or hydrogenated after aldol condensation and the like to be transformed into various acids and alcohols containing long alkyl groups. Particularly, hydrogenated alcohols of aldehydes produced by such oxo reaction are called oxo alcohols. Such oxo alcohol is industrially, widely used as a solvent, an additive, a raw material of various plasticizers, a synthetic lubricating oil, and the like.

In this regard, since the ratio of linear aldehyde (normal-aldehyde) derivatives among aldehydes produced by the oxo reaction is high, most research into catalysts has focused on increasing the proportion of the linear aldehyde derivatives. However, in recent years, demand for iso-aldehydes has increased due to development of, for example, isobutyric acid, neopentyl glycol (NPG), 2,2,4-trimethyl-1,3-pentanediol, isovaleric acid, and the like, which use a branched aldehyde derivative (iso-aldehyde) as a raw material, and thus, research to increase selectivity for branched aldehyde derivatives is underway. Accordingly, there is a need for development of a catalyst having superior stability and activity while lowering an n/i ratio in aldehyde.

Related Art Document

[Patent Document](Patent Document 1) US4215077 A

DISCLOSURE

Technical Problem

Therefore, the present invention has been made in view of the above problems, and it is one object of the present invention to provide a catalyst composition for hydroformylation which increases productivity and provides superior catalytic activity and stability while lowering an n/i ratio in generated aldehyde upon hydroformylation of an olefinic compound.

It is another object of the present invention to provide a method of hydroformylating an olefinic compound using the catalyst composition.

The above and other objects can be accomplished by the present invention described below.

Technical Solution

In accordance with an aspect of the present invention, the above and other objects can be accomplished by the provision of a catalyst composition for hydroformylation, including a phosphoramidite ligand represented by Formula 1 below and a transition metal catalyst:

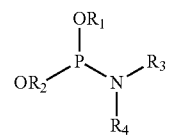

[Formula 1]

wherein $R_1$, $R_2$ and $R_4$ are connected to each other; one group selected from among $R_1$, $R_2$, and $R_4$ is a $C_1$ to $C_3$ substituted hydrocarbon group (CH) or tertiary amine group (N); the remaining two groups, except for the group selected from among $R_1$, $R_2$, and $R_4$, are each independently a $C_1$ to $C_{20}$ alkylene group, $C_5$ to $C_{20}$ cycloalkylene group, $C_6$ to $C_{20}$ arylene group, or $C_6$ to $C_{20}$ alkylarylene group; and $R_3$ is hydrogen, a primary amine group ($NH_2$), a $C_1$ to $C_{20}$ alkyl group, a $C_5$ to $C_{20}$ cyclo alkyl group, a $C_6$ to $C_{20}$ aryl group or a $C_6$ to $C_{20}$ alkylaryl group.

In accordance with another aspect of the present invention, there is provided a method of hydroformylating an olefinic compound, the method including a step of preparing aldehyde by reacting an olefinic compound with a syngas of carbon monoxide and hydrogen ($CO/H_2$) in the presence of the catalyst composition for hydroformylation.

Advantageous effects

As apparent from the above description, the present invention provides a catalyst composition for hydroformylation which increases productivity and provides superior catalytic activity and stability while lowering an n/i ratio in generated aldehyde upon hydroformylation of an olefinic compound, and a method of hydroformylating an olefinic compound using the catalyst composition.

DESCRIPTION OF DRAWINGS

FIG. 1 illustrates comparative results of catalyst stability and productivity of Examples 2 and 7 according to the present invention and Comparative Examples 1 and 2.

BEST MODE

Hereinafter, the present invention is described in detail.

The present inventors confirmed that, when a phosphoramidite ligand, which is electronically enriched and has high steric hindrance, is applied to a catalyst composition used in hydroformylation of olefin, an n/i ratio in aldehyde is lowered, productivity increases, and superior catalytic activity and stability are provided, compared to conventional catalyst compositions to which a phosphine or phosphite ligand is applied, thus completing the present invention.

The catalyst composition for hydroformylation according to the present invention includes a phosphoramidite ligand and a transition metal catalyst.

Hereinafter, each constituent of the catalyst composition is described in detail.

The phosphoramidite may be, for example, a phosphoramidite represented by Formula 1 below:

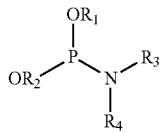

[Formula 1]

In Formula 1, $R_1$, $R_2$ and $R_4$ may be connected to each other; one group selected from among $R_1$, $R_2$, and $R_4$ may be a $C_1$ to $C_3$ substituted hydrocarbon group (CH) or tertiary amine group (N); the remaining two groups, except for the group selected from among $R_1$, $R_2$, and $R_4$, may be each independently a $C_1$ to $C_{20}$ alkylene group, $C_5$ to $C_{20}$ cycloalkylene group, $C_6$ to $C_{20}$ arylene group, or $C_6$ to $C_{20}$ alkylarylene group; and $R_3$ may be hydrogen, a primary amine group ($NH_2$), a $C_1$ to $C_{20}$ alkyl group, a $C_5$ to $C_{20}$ cyclo alkyl group, a $C_6$ to $C_{20}$ aryl group or a $C_6$ to $C_{20}$ alkylaryl group. Alternatively, $R_1$, $R_2$ and $R_4$ may be connected to each other; one group selected from among $R_1$, $R_2$, and $R_4$ may be a $C_1$ to $C_3$ substituted hydrocarbon group (CH); the remaining two groups, except for the group selected from among $R_1$, $R_2$, and $R_4$, may be each independently a $C_1$ to $C_{10}$ alkylene group, $C_5$ to $C_{15}$ cycloalkylene group, $C_6$ to $C_{15}$ arylene group, or $C_6$ to $C_{15}$ alkylarylene group; and $R_3$ may be hydrogen, a primary amine group ($NH_2$), a $C_1$ to $C_{10}$ alkyl group, a $C_5$ to $C_{15}$ cyclo alkyl group, a $C_6$ to $C_{15}$ aryl group or a $C_6$ to $C_{15}$ alkylaryl group.

As a specific example, the phosphoramidite represented by Formula 1 may be a bicyclic phosphoramidite represented by Formula 2 below:

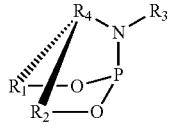

[Formula 2]

In Formula 2, $R_1$ and $R_2$ may be each independently a $C_1$ to $C_{20}$ alkylene group, $C_5$ to $C_{20}$ cycloalkylene group, $C_6$ to $C_{20}$ arylene group, or $C_6$ to $C_{20}$ alkylarylene group; $R_3$ may be a $C_1$ to $C_{20}$ alkyl group, $C_5$ to $C_{20}$ cyclo alkyl group, $C_6$ to $C_{20}$ aryl group, or $C_6$ to $C_{20}$ alkylaryl group; and $R_4$ may be a $C_1$ to $C_3$ substituted hydrocarbon group (CH) or tertiary amine group (N). Alternatively, $R_1$ and $R_2$ may be each independently a $C_1$ to $C_{10}$ alkylene group, $C_5$ to $C_{15}$ cycloalkylene group, $C_6$ to $C_{15}$ arylene group, or $C_6$ to $C_{15}$ alkylarylene group; $R_3$ may be a $C_1$ to $C_{15}$ alkyl group, $C_5$ to $C_{15}$ cyclo alkyl group, $C_6$ to $C_{15}$ aryl group, or $C_6$ to $C_{15}$ alkylaryl group; and $R_4$ may be a $C_1$ to $C_3$ substituted hydrocarbon group (CH). In this case, superior catalytic activity and stability are exhibited and superior productivity is provided.

The phosphoramidite ligand may be, for example, a mono-coordinate ligand.

The phosphoramidite ligand may be included in an amount of, for example, 0.1 to 10% by weight, 0.1 to 6% by weight, 0.1 to 3% by weight, or 0.1 to 1.5% by weight based on the weight of the catalyst composition. Within this range, superior catalytic activity and stability are exhibited and a normal/iso (n/i) ratio in aldehyde is lowered.

The phosphoramidite ligand may be included in a mole fraction of, for example, 1 to 500, 5 to 100, or 10 to 100 based on 1 mole of a transition metal of the transition metal catalyst. Within this range, superior catalytic activity and stability are provided.

The transition metal catalyst may be, for example, a transition metal catalyst represented by Formula 3 below:

$$M(L^1)_x(L^2)_y(L^3)_z$$ [Formula 3]

In Formula 3, M may be one selected from the group consisting of cobalt (Co), rhodium (Rh), iridium (Ir), ruthenium (Ru), iron (Fe), nickel (Ni), palladium (Pd), platinum (Pt), and osmium (Os); each of $L^1$, $L^2$ and $L^3$ may be independently one selected from the group consisting of hydrogen, carbonyl (CO), cyclooctadiene, norbornene, chlorine, triphenylphosphine (TPP) and acetylacetonato (AcAc); and x, y and z may be each independently 0 to 5, but x, y and z might not all be 0.

As a specific example, the transition metal catalyst may be one or more selected from the group consisting of cobaltcarbonyl [$Co_2(CO)_8$], acetylacetonatodicarbonylrhodium [$Rh(AcAc)(CO)_2$], rhodium acetylacetonato carbonyl triphenylphosphine [$Rh(AcAc)(CO)(TPP)$], hydridocarbonyltri(triphenylphosphine)rhodium [$HRh(CO)(TPP)_3$], acetylacetonatodicarbonyliridium [$Ir(AcAc)(CO)_2$], and hydridocarbonyltri (triphenylphosphine) iridium [$HIr(CO)(TPP)_3$]. In this case, superior catalytic activity is provided.

The content of the transition metal catalyst may be, for example, 1 to 1,000 ppm, 10 to 800 ppm, or 10 to 300 ppm based on the catalyst composition. Within this range, the rate of hydroformylation is excellent.

The catalyst composition for hydroformylation may further include one or more solvents selected from the group consisting of propane aldehyde, butyl aldehyde, pentyl aldehyde, valer aldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane. In this case, suerior catalyst stability is exhibited.

A hydroformylation method according to the present invention includes a step of preparing aldehyde by reacting an olefinic compound with a syngas of carbon monoxide and hydrogen ($CO/H_2$) in the presence of the catalyst composition for hydroformylation.

The olefinic compound may be, for example, a compound represented by Formula 4 below:

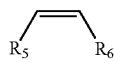

[Formula 4]

In Formula 4, $R_5$ and $R_6$ may be each independently hydrogen, a $C_1$ to $C_{20}$ alkyl group, fluorine (F), chlorine (Cl), bromine (Br), trifluoromethyl ($-CF_3$), or a $C_6$ to $C_{20}$ aryl group having 0 to 5 substituents, and the substituents of the $C_6$ to $C_{20}$ aryl group may be nitro ($-NO_2$), fluorine (F), chlorine (Cl), bromine (Br), methyl, ethyl, propyl, or butyl.

As a specific example, the olefinic compound may be one or more selected from the group consisting of ethene, propene, 1-butene, 1-pentene, 1-hexene, 1-octene and styrene.

A mix ratio of hydrogen to carbon monoxide in the syngas ($CO/H_2$) may be, for example, 5:95 to 70:30, 40:60 to 60:40, or 45:55 to 55:45 in a mole ratio. Within this range, gases used for the reaction do not accumulate in a reactor, whereby the reactivity of the catalyst is excellent.

In the hydroformylation, a reaction temperature between the olefinic compound and the syngas ($CO/H_2$) in the presence of the catalyst composition may be, for example, 20 to 180° C., 50 to 150° C., or 60 to 100° C. Within this range, the stability and activity of the catalyst are maintained during the hydroformylation.

In another embodiment, in the hydroformylation, a reaction pressure in a reactor may be 1 to 100 bar, 1 to 50 bar, or 5 to 30 bar. Within this range, superior catalytic activity is provided.

The method of hydroformylating an olefinic compound may be represented by, for example, Reaction Formula 1 below:

[Reaction Formula 1]

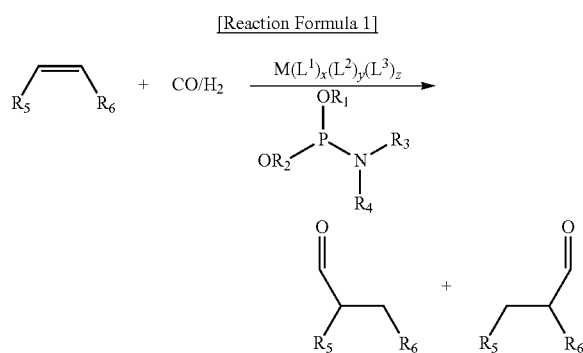

As a specific example, the transition metal catalyst represented by Formula 3 and the phosphoramidite ligand represented by Formula 1 are dissolved in the solvent to prepare a mixture including the transition metal catalyst and the phosphoramidite ligand. Subsequently, the mixture is fed into a general reactor along with the olefinic compound represented by Formula 4 and the syngas ($CO/H_2$). While stirring a resultant mixture, temperature and pressure are elevated such that hydroformylation is performed. As a result, aldehyde may be prepared.

An n/i ratio in aldehyde prepared by the method of hydroformylating an olefinic compound may be, for example, 6.5 or less, 1.0 to 6.5, 1.5 to 4.0, or 1.5 to 3.0.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLES

Example 1 to 10 and Comparative Examples 1 to 7

24.37 μmol of rhodium acetylacetonato carbonyl triphenylphosphine (Rh(AcAc)(CO)(TPP), ROPAC), as a catalyst, was dissolved with a ligand in an amount of % by weight summarized in Table 1 below in valeraldehyde as a solvent such that a total amount of resultant solution became 10 ml (Rh 250 ppm). Subsequently, the resultant solution was fed into a 20 ml autoclave reactor in High Throughput Screen apparatus (HTS, manufactured by Autoclave, US, 10 reactions can be simultaneously performed in this multiclave apparatus). To this reaction solution, a mix gas in which propylene ($C_3H_6$) and a syngas($CO/H_2$) were mixed in a mole ratio of 1:1:1 ($C_3H_6:CO:H_2$) was injected, the pressure in the reactor was maintained at 8 bar, and reaction was performed at 90° C. for 4 hours and 15 minutes while stirring.

Test example

With regard to the catalyst composition prepared according to each of Examples 1 to 10 and Comparative Examples to 7, an n/i ratio in aldehyde, catalytic activity and stability, and productivity were measured according to the following methods. Results are summarized in Tables 1 and 2 below.

Measurement Methods

※ n/i ratio in aldehyde: Obtained by dividing the amount of generated n-butyraldehyde by the amount of iso-butyraldehyde. A generation amount of each aldehyde was determined by gas chromatography (GC) analysis after reaction.

※Catalytic activity (normal activity, %): With respect to 100% by weight of normal and isobutyl aldehyde generated by adding a mixed gas, which included propylene ($C_3H_6$) and a syngas ($CO/H_2$) in a mole ratio of 1:1:1 ($C_3H_6:CO:H_2$), to a reaction solution prepared according to Comparative Example 1, by maintaining the pressure in a reactor at 8 bar, and reacting at 90° C. for one hour while stirring, a total weight of normal and isobutyl aldehyde generated by reacting, under the same conditions, a reaction solution of each of the examples and comparative examples was compared and expressed as a percentage according to Equation 1 below:

Catalytic activity=total weight of normal and isobutyl aldehyde of each of the examples or the comparative examples/total weight of normal and isobutyl aldehyde of Comparative Example 1×100   [Equation 1]

※Color after reaction: the color of the catalyst solution of each of the examples and the comparative examples after reaction was observed with the naked eye.

TABLE 1

| Classification | Catalyst(Rh) | Ligand | Ligand content | Ration of n/i | Catalytic activity | Color after reaction |
|---|---|---|---|---|---|---|
| Example 1 | ROPAC | Phosphoramidite-1 | 0.5% by weight | 1.8 | 422 | Brown |

TABLE 1-continued

| Classification | Catalyst(Rh) | Ligand | Ligand content | Ration of n/i | Catalytic activity | Color after reaction |
|---|---|---|---|---|---|---|
| Example 2 | ROPAC | Phosphoramidite-1 | 1% by weight | 2.8 | 503 | Light yellow |
| Example 3 | ROPAC | Phosphoramidite-1 | 3% by weight | 5.7 | 167 | Light yellow |
| Example 4 | ROPAC | Phosphoramidite-1 | 5% by weight | 6.2 | 130 | Yellow |
| Example 5 | ROPAC | Phosphoramidite-1 | 6% by weight | 6.5 | 126 | Yellow |
| Example 6 | ROPAC | Phosphoramidite-2 | 0.5% by weight | 1.6 | 474 | Brown |
| Example 7 | ROPAC | Phosphoramidite-2 | 1% by weight | 2.5 | 196 | Light yellow |
| Example 8 | ROPAC | Phosphoramidite-2 | 3% by weight | 3.7 | 140 | Yellow |
| Example 9 | ROPAC | Phosphoramidite-2 | 5% by weight | 5.1 | 110 | Yellow |
| Example 10 | ROPAC | Phosphoramidite-2 | 6% by weight | 5.5 | 90 | Yellow |
| Comparative Examples 1 | ROPAC | TPP | 6% by weight | 10 | 100 | Dark yellow |
| Comparative Examples 2 | ROPAC | TPP | 3% by weight | 6.7 | 135 | Yellow |
| Comparative Examples 3 | ROPAC | TPTP | 2% by weight | 3.7 | 120 | Yellow |
| Comparative Examples 4 | ROPAC | TPTP | 3% by weight | 4.2 | 100 | Dark yellow |
| Comparative Examples 5 | ROPAC | DPPB | 2% by weight | 2.5 | 47 | Brown |
| Comparative Examples 6 | ROPAC | DPPH | 2% by weight | 6.4 | 31 | Dark Brown |
| Comparative Examples 7 | ROPAC | CDTP | 2% by weight | 1.7 | 37 | Dark Brown |

※ Phosporamidite-1: 12H-Dibenzo[d,g][1,3,2]dioxaphosphocin-6,12-imine, 13-phenyl-(Cas. No. 1630816-45-3)

※ Phosphoramidite-2: 12H-Dibenzo[d,g][1,3,2]dioxaphosphocin-6,12-imine, 13-(3,5-dimethylphenyl)-(Cas. No. 1630816-46-4)

※ TPP: triphenylphosphine
※ TPTP: tri-p-tolylphosphine
※ DPPB: 1,4-Bis(diphenylphosphino)butane
※ DPPH: 1,6-Bis(diphenylphosphino)hexane
※ CDTP: Cyclohexyl-di-p-tolylphosphine

[Additional Test Example]

※ Catalyst stability (normal stability, aging) and productivity (%): The rhodium acetylacetonato carbonyl triphenylphosphine (Rh(AcAc)(CO)(TPP), ROPAC) and ligand of each of Examples 2 and 7 and Comparative Examples 1 to 4 were included in the same amounts as in Example 1, and dissolved in n-butyraldehyde, as a solvent, such that a total weight of resultant solution was 100 g (Rh 250 ppm). The resultant solution was fed into a 600 ml autoclave reactor. A syngas ($CO/H_2$), which included CO and $H_2$ in a mole ratio of 1:1, was injected into the resultant solution such that the pressure inside the reactor became 6 bar, and stirring was performed for 0, 2.5 hours, 5 hours, or 15 hours at 120° C., followed by cooling up to 20° C. Subsequently, the syngas was replaced with a mixed gas in which propylene ($C_3H_6$) and the syngas ($CO/H_2$) were mixed in a mole ratio of 1:1:1 ($C_3H_6:CO:H_2$). Subsequently, the pressure inside the reactor was maintained at 8 bar and reaction was allowed to proceed at 90° C. for one hour. Resultant productivity was expressed as a consumed amount of the mixed gas in which propylene ($C_3H_6$) and the syngas ($CO/H_2$) were mixed in a mole ratio of 1:1:1 ($C_3H_6:CO:H_2$). Improved catalyst stability results in improved productivity.

TABLE 2

| | Productivity (catalyst stability) Elapsed time | | | |
|---|---|---|---|---|
| Classification | 0 hr | 2.5 hr | 5 hr | 15 hr |
| Example 2 (Phosphoramidite - 11% by weight) | 510 | 465 | 423 | 370 |
| Example 7 (Phosphoramidite - 21% by weight) | 667 | 616 | 573 | 526 |
| Comparative Examples 1 (TPP - 6% by weight) | 100 | 52 | 48 | 37 |
| Comparative Examples 2 (TPP - 3% by weight) | 142 | 52 | 44 | 26 |
| Comparative Examples 3 (TPTP - 2% by weight) | 137 | 80 | 68 | 39 |
| Comparative Examples 4 (TPTP - 3% by weight) | 173 | 68 | 57 | 23 |

As summarized in Table 1, it can be confirmed that the catalyst compositions of Examples 1 to 10 prepared according to the present invention exhibit superior catalytic activity while maintaining an n/i ratio in aldehyde within a proper range. In addition, as shown in Table 2, it can be confirmed that productivity decrease over time of the catalyst compositions of the present invention is very small, which indicates superior catalyst stability (see the comparative graph of FIG. 1). Further, from the color results after reaction, it can be confirmed that, when the ligands of the present invention are included in a predetermined amount or more, deactivation degrees of the catalyst solutions after reaction are small.

On the other hand, it can be confirmed that, in Comparative Examples 1 and 2 including triphenylphosphine as a ligand and Comparative Examples 3 and 4 including tri-p-tolylphosphine as a ligand, an n/i ratio in aldehyde is high and productivity and catalyst stability are poor (see the comparative graph of FIG. 1). In addition, it can be confirmed that, in Comparative Examples 5 including 1,4-bis(diphenylphosphino)butane as a ligand, Comparative Examples 6 including 1,6-bis(diphenylphosphino)hexane as a ligand, and Comparative Examples 7 including cyclohexyl-di-para-tolylphosphine as a ligand, catalytic activity is very poor.

In conclusion, the present inventors confirmed that, when the phosphoramidite ligand of the present invention is applied, the activity and stability of the catalyst may be maintained by the ligand which is electronically enriched and has high steric hindrance. In addition, by using the catalyst composition, an n/i ratio in generated aldehyde upon hydroformylation of an olefinic compound may be remarkably reduced.

The invention claimed is:

1. A catalyst composition for hydroformylation, comprising a bicyclic phosphoramidite ligand represented by Formula 2 below and a transition metal catalyst:

[Formula 2]

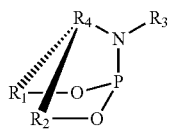

wherein $R_1$ and $R_2$ are each independently a $C_1$ to $C_{20}$ alkylene group, $C_5$ to $C_{20}$ cycloalkylene group, $C_6$ to $C_{20}$ arylene group, or $C_6$ to $C_{20}$ alkylarylene group; $R_3$ is a $C_1$ to $C_{20}$ alkyl group, $C_5$ to $C_{20}$ cyclo alkyl group, $C_6$ to $C_{20}$ aryl group, or $C_6$ to $C_{20}$ alkylaryl group; and $R_4$ is a $C_1$ to $C_3$ substituted hydrocarbon group (CH), wherein the transition metal catalyst is one or more selected from the group consisting of cobaltcarbonyl $[Co_2(CO)_8]$, acetylacetonatodicarbonylrhodium $[Rh(AcAc)(CO)_2]$, rhodium acetylacetonato carbonyl triphenylphosphine $[Rh(AcAc)(CO)(TPP)]$, hydridocarbonyltri(triphenylphosphine)rhodium $[HRh(CO)(TPP)_3]$, acetylacetonatodicarbonyliridium $[Ir(AcAc)(CO)_2]$, and hydridocarbonyltri(triphenylphosphine)iridium $[HIr(CO)(TPP))_3]$.

2. The catalyst composition according to claim 1, wherein the phosphoramidite ligand is comprised in an amount of 0.1 to 10% by weight based on a weight of the catalyst composition.

3. The catalyst composition according to claim 1, wherein a molar fraction of the phosphoramidite ligand is 1 to 500 based on 1 mole of a transition metal of the transition metal catalyst.

4. The catalyst composition according to claim 1, wherein a content of the transition metal catalyst is 1 to 1,000 ppm based on the catalyst composition for hydroformylation.

5. The catalyst composition according to claim 1, wherein the catalyst composition for hydroformylation further comprises one or more solvents selected from the group consisting of propane aldehyde, butyl aldehyde, pentyl aldehyde, valer aldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane.

6. A method of hydroformylating an olefinic compound, the method comprising a step of preparing AN aldehyde by reacting an olefinic compound with a syngas of carbon monoxide and hydrogen $(CO/H_2)$ in the presence of the catalyst composition for hydroformylation according to claim 1.

7. The method according to claim 6, wherein the olefinic compound is a compound represented by Formula 4 below:

[Formula 4]

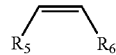

wherein $R_5$ and $R_6$ are each independently hydrogen, a $C_1$ to $C_{20}$ alkyl group, fluorine (F), chlorine (Cl), bromine (Br), trifluoromethyl (—$CF_3$), or a $C_6$ to $C_{20}$ aryl group having 0 to 5 substituents, and the substituents of the $C_6$ to $C_{20}$ aryl group are nitro (—$NO_2$), fluorine (F), chlorine (Cl), bromine (Br), methyl, ethyl, propyl, or butyl.

8. The method according to claim 6, wherein the olefinic compound is one or more selected from the group consisting of ethene, propene, 1-butene, 1-pentene, 1-hexene, 1-octene and styrene.

9. The method according to claim 6, wherein a normal/iso (n/i) ratio in the prepared aldehyde is 6.5 or less.

10. The method according to claim 6, wherein a mix ratio of hydrogen to carbon monoxide in the syngas $(CO/H_2)$ is 5:95 to 70:30 in a mole ratio.

* * * * *